(12) United States Patent
Colorado, Jr. et al.

(10) Patent No.: US 9,266,797 B2
(45) Date of Patent: Feb. 23, 2016

(54) ONLINE MONITORING OF POLYMERIZATION INHIBITORS FOR CONTROL OF UNDESIRABLE POLYMERIZATION

(71) Applicant: Ecolab USA Inc., Naperville, IL (US)

(72) Inventors: Ramon Colorado, Jr., Houston, TX (US); Vincent Lewis, Rosenberg, TX (US); Robert A. Geiger, Richmond, TX (US); Jessica Hancock, Zaandam (NL); Andrew R. Neilson, Richmond, TX (US)

(73) Assignee: Ecolab USA Inc., St. Paul, MN (US)

( * ) Notice: Subject to any disclaimer, the term of this patent is extended or adjusted under 35 U.S.C. 154(b) by 225 days.

(21) Appl. No.: 13/765,508

(22) Filed: Feb. 12, 2013

(65) Prior Publication Data

US 2014/0228604 A1    Aug. 14, 2014

(51) Int. Cl.
*C07C 2/04*    (2006.01)
*C07C 7/20*    (2006.01)
*C08F 2/38*    (2006.01)

(52) U.S. Cl.
CPC ... *C07C 7/20* (2013.01); *C08F 2/38* (2013.01); *C08F 2438/02* (2013.01)

(58) Field of Classification Search
USPC .................. 585/950, 956, 440, 435, 502, 422; 203/8
See application file for complete search history.

(56) References Cited

U.S. PATENT DOCUMENTS

| | | | |
|---|---|---|---|
| 4,360,776 A | 11/1982 | Bauman | |
| 4,415,671 A | 11/1983 | Nicksic | |
| 4,531,093 A | 7/1985 | Rollwitz et al. | |
| 4,536,711 A | 8/1985 | King et al. | |
| 4,593,248 A | 6/1986 | Hyde et al. | |
| 4,783,314 A | 11/1988 | Hoots et al. | |
| 4,966,711 A | 10/1990 | Hoots et al. | |
| 4,992,380 A | 2/1991 | Moriarty et al. | |
| 5,006,311 A | 4/1991 | Hoots et al. | |
| 5,041,386 A | 8/1991 | Pierce et al. | |
| 5,120,661 A | 6/1992 | Baker | |
| 5,132,096 A | 7/1992 | Hoots et al. | |
| 5,166,074 A | 11/1992 | Vessey et al. | |
| 5,171,450 A | 12/1992 | Hoots et al. | |
| 5,200,106 A | 4/1993 | Hoots et al. | |
| 5,233,303 A | 8/1993 | Bales et al. | |
| 5,236,845 A | 8/1993 | Pierce et al. | |
| 5,242,602 A | 9/1993 | Richardson et al. | |
| 5,266,493 A | 11/1993 | Young | |
| 5,277,135 A | 1/1994 | Dubin et al. | |
| 5,278,074 A | 1/1994 | Rao et al. | |
| 5,282,379 A | 2/1994 | Harder et al. | |

(Continued)

FOREIGN PATENT DOCUMENTS

JP    2003524034    8/2003
JP    2012077041    4/2012

*Primary Examiner* — Thuan D Dang
(74) *Attorney, Agent, or Firm* — Eric D. Babych; Brinks Gilson & Lione

(57) ABSTRACT

Disclosed herein are systems and methods for monitoring and controlling a nitroxide-based polymerization inhibitor in vinyl-based monomers. A dosage of the nitroxide-based polymerization inhibitor is provided in the vinyl-based monomers. A residual concentration of the nitroxide-based polymerization inhibitor is measured substantially in real time, and an optimized dosage of the nitroxide-based polymerization inhibitor is provided in response to the measured residual concentration.

13 Claims, 15 Drawing Sheets

(56) References Cited

U.S. PATENT DOCUMENTS

| | | |
|---|---|---|
| 5,343,150 A | 8/1994 | Nakahata et al. |
| 5,389,548 A | 2/1995 | Hoots et al. |
| 5,494,030 A | 2/1996 | Swartz et al. |
| 5,652,147 A | 7/1997 | Kawamura et al. |
| 5,706,805 A | 1/1998 | Swartz et al. |
| 5,833,601 A | 11/1998 | Swartz et al. |
| 6,046,587 A | 4/2000 | King et al. |
| 6,153,110 A | 11/2000 | Richardson et al. |
| 6,462,546 B1 | 10/2002 | Schmalbein et al. |
| 6,510,368 B1 | 1/2003 | Beardwood et al. |
| 6,587,753 B2 | 7/2003 | Fowee |
| 6,790,664 B2 | 9/2004 | Bailey et al. |
| 7,084,628 B2 | 8/2006 | Swartz et al. |
| 7,220,382 B2 | 5/2007 | Godfrey et al. |
| 7,403,008 B2 | 7/2008 | Blank et al. |
| 7,589,529 B1 | 9/2009 | White et al. |
| 7,868,616 B2 | 1/2011 | White et al. |
| 8,125,224 B2 | 2/2012 | White et al. |
| 8,212,563 B2 | 7/2012 | White et al. |
| 8,648,596 B2 | 2/2014 | Elliott et al. |
| 9,103,261 B1 | 8/2015 | White et al. |
| 2002/0048820 A1 | 4/2002 | Onishi et al. |
| 2003/0080318 A1* | 5/2003 | Benage et al. ............ 252/182.18 |
| 2003/0095471 A1 | 5/2003 | Hamamoto et al. |
| 2003/0155916 A1 | 8/2003 | Maier et al. |
| 2005/0004413 A1* | 1/2005 | Kanauchi et al. ............. 585/810 |
| 2005/0245696 A1* | 11/2005 | Cole et al. ....................... 526/72 |
| 2010/0162816 A1 | 7/2010 | Thoret et al. |
| 2012/0130119 A1 | 5/2012 | Salisbury et al. |

* cited by examiner

ONLINE MONITORING OF POLYMERIZATION INHIBITORS FOR CONTROL OF UNDESIRABLE POLYMERIZATION

TECHNICAL FIELD

This invention relates generally to systems and methods for the online monitoring of polymerization inhibitors for control of undesirable polymerization. More specifically, the invention relates to systems and methods of monitoring and controlling a nitroxide-based polymerization inhibitor in a vinyl-based monomer. The invention has particular relevance to locally and/or globally monitoring and controlling undesirable polymerization in downstream petrochemical systems.

BACKGROUND

Many vinyl-based monomers are prone to spontaneous undesirable polymerization during manufacturing and purification, as well as during handling, transportation, and storage. For example, the vinyl-based monomers can react under the heat used in manufacturing and purification to undesirably form highly crosslinked polymers. These polymers may form foamy or crusty granules that ultimately plug production lines and equipment, and thereby may potentially cause physical damage.

Nitroxide-based compounds can inhibit the undesirable polymerization of vinyl-based monomers. In particular, nitroxide-based compounds can be fast-acting inhibitors, and can be used alone or in combination with slower-acting polymerization retarders or antioxidants. To minimize the undesirable polymerization of the vinyl-based monomers, an optimized dosage of nitroxide-based inhibitors may need to be continuously provided into the liquid phase of the vinyl-based monomers during manufacturing and purification. There thus exists an ongoing need to develop systems and methods of monitoring a residual concentration of the nitroxide-based inhibitors substantially in real time at any given point in time so as to immediately provide an optimized dosage of the nitroxide-based inhibitor during a manufacturing process without interruption.

SUMMARY

This disclosure accordingly provides systems and methods for monitoring and controlling a nitroxide-based polymerization inhibitor in vinyl-based monomers, substantially in real time. The online monitoring of nitroxide-based inhibitor concentration can be correlated to an extent of undesirable polymerization. Moreover, the online monitoring of nitroxide-based inhibitor concentration can be used as an indirect probe of additional factors affecting the overall polymerization kinetics, such as the dosage of secondary slower-acting polymerization retarders or antioxidants.

In an aspect, the invention provides a method of monitoring and controlling a nitroxide-based polymerization inhibitor in vinyl-based monomers. The method includes providing a dosage of the nitroxide-based polymerization inhibitor in the vinyl-based monomers. A residual concentration of the nitroxide-based polymerization inhibitor is measured substantially in real time, and an optimized dosage of the nitroxide-based polymerization inhibitor is provided in response to the measured residual concentration.

In another aspect, the invention provides a system for monitoring and controlling undesirable polymerization in vinyl-based monomers. The system includes a fast flow sampling loop, and a control module connected to the fast flow sampling loop. The control module is capable of controlling sample conditioning and measuring a residual concentration of a nitroxide-based polymerization inhibitor in the vinyl-based monomers substantially in real time.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

DETAILED DESCRIPTION

Figure 1:
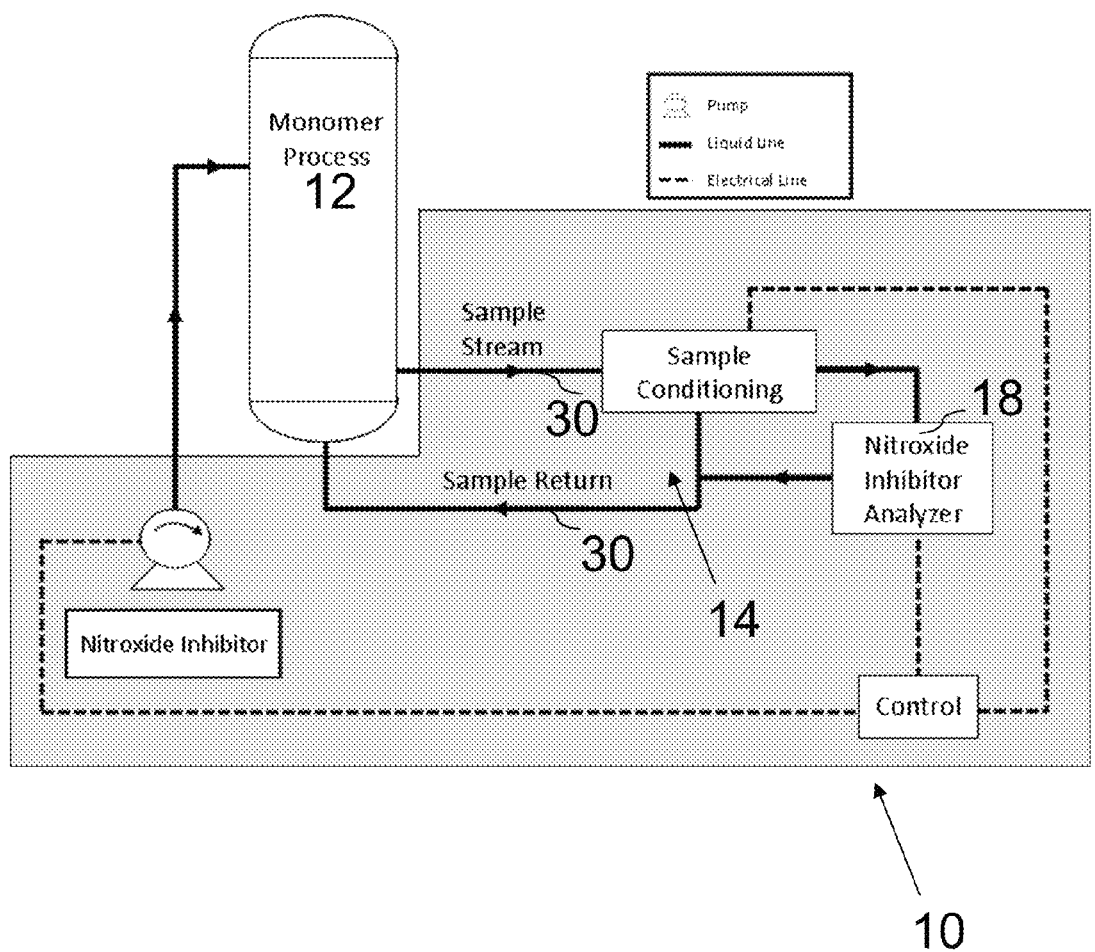
FIG. 1 is a schematic illustration of a system according to one embodiment of the invention for monitoring and controlling a residual concentration of a nitroxide-based inhibitor in vinyl-based monomers.

Described herein are systems and methods for monitoring and controlling a nitroxide-based polymerization inhibitor in vinyl-based monomers, substantially in real time. The systems and methods can be advantageous in inhibiting undesirable polymerization. The system includes a fast flow sampling loop, an enclosure connected to the fast flow sampling loop, and a control module positioned within the enclosure. The control module is capable of controlling sample conditioning and measuring a residual concentration of a nitroxide-based polymerization inhibitor in the vinyl-based monomers substantially in real time.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, for the recitation of numeric ranges herein, each intervening number therebetween with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, "monomers" refers to olefinic hydrocarbons, dienes, vinyl aromatic monomers, halogenated monomers, unsaturated acids, unsaturated esters, unsaturated amides, unsaturated nitriles, unsaturated ethers, acrylated urethanes, unsatured polyesters and mixtures thereof. For example, the monomers may include ethylene, propylene, 1,3-butadiene, chloroprene, butenes, isoprene, C4-C30 α-olefins, styrene, α-methylstyrene, vinyltoluene, divinylbenzene, styrene sulfonic acid, 2,4-dichloro styrene, vinyl naphthalene, diisopropenyl benzene, vinyl chloride, acrylic acid, methacrylic acid, vinyl acetate, 2-hydroxyethyl acrylate, 2-hydroxyethyl methacrylate, trimethylolpropane triacrylate, polyethylene glycol diacrylate, methyl methacrylate, butyl methyacrylate, and structural isomers, derivatives of said compounds and mixtures thereof.

As used herein, "nitroxide-based inhibitor" refers to stable nitroxide free-radical compounds (SNFR) having the generic structure:

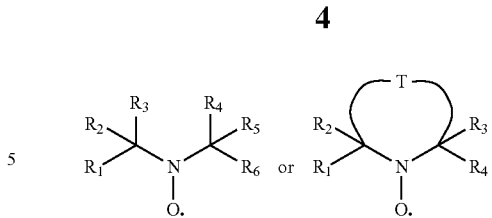

where each R is alkyl or aryl and T is a group required to complete a 5- or 6-membered ring. For example, the nitroxide-based inhibitor may include 4-hydroxyl-2,2,6,6-tetramethylpiperidine-1-oxyl or its 4-substituted-2,2,6,6-tetramethylpiperidine-1-oxyl homologs. Likewise, the following corresponding hydroxyl amines or other homologs of these SNFRs which could form an SNFR in situ are contemplated for use as a nitroxide-based inhibitor.

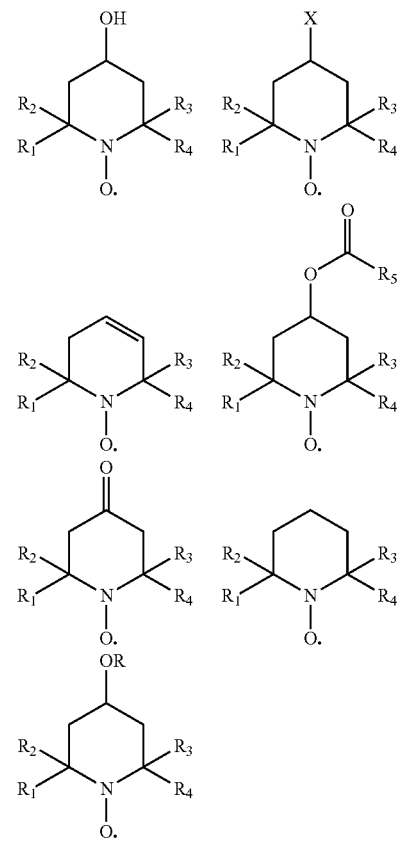

Moreover, in some nitroxide-based inhibitors, two or more nitroxyl groups may be present in the same molecule by being linked through the T moiety as exemplified below where E is a linking group, such as diacids, diesters, diamides, diols, diamines, or triazines.

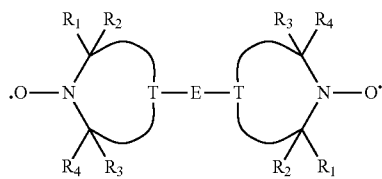

-continued

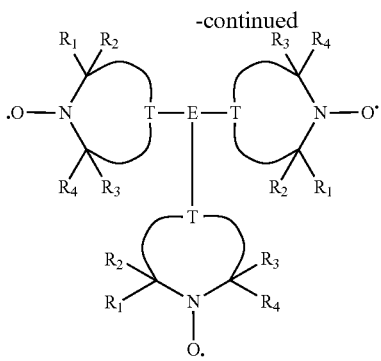

Furthermore, the nitroxide-based inhibitor may include the following nitroxides: di-tert-butyl nitroxyl, 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, 1-oxyl-2,2,6,6-tetramethyl-4-n-propoxypiperidine, 1-oxyl-2,2,6,6-tetramethyl-4-n-butoxypiperidine, 1-oxyl-2,2,6,6-tetramethyl-4-t-butoxypiperidine, 1-oxyl-2,2,6,6-tetramethyl-4-s-butoxypiperidine, 1-oxyl-2,2,6,6-tetramethyl-4-(2-methoxyethoxy)piperidine, 1-oxyl-2,2,6,6-tetramethyl-4-(2-methoxyethoxyacetoxy)piperidine, 1-oxyl-2,2,6,6-tetramethylpiperidin-4-yl stearate, 1-oxyl-2,2,6,6-tetramethylpiperidin-4-yl acetate, 1-oxyl-2,2,6,6-tetramethylpiperidin-4-yl butyrate, 1-oxyl-2,2,6,6-tetramethylpiperidin-4-yl 2-ethylhexanoate, 1-oxyl-2,2,6,6-tetramethylpiperidin-4-yl octanoate, 1-oxyl-2,2,6,6-tetramethylpiperidin-4-yl laurate, 1-oxyl-2,2,6,6-tetramethylpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, 1-oxyl-2,2,6,6-tetramethyl-4-allyloxy-piperidine, 1-oxyl-2,2,6,6-tetramethyl-4-acetamidopiperidine, 1-oxyl-2,2,6,6-tetramethyl-4-(N-butylformamido)piperidine, N,N'-bis(1-oxyl-2,2,6,6-tetramethylpiperidin-4-yl) adipamide, N-(1-oxyl-2,2,6,6-tetramethylpiperidin-4-yl)-caprolactam, N-(1-oxyl-2,2,6,6-tetramethylpiperidin-4-yl)-dodecylsuccinimide, 2,4,6-tris-[N-butyl-N-(1-oxyl-2,266-tetramethylpiperidin-4-yl)]-s-triazine, 2,4,6-tris-[N-(1-oxyl-2,2,6,6-tetramethylpiperidin-4-yl)]-s-triazine, 4,4'-ethylenebis(1-oxyl-2,2,6,6-tetramethylpiperazin-3-one), 1-oxyl-2,2,6,6-tetramethyl-4-(2,3-dihydroxypropoxy)piperidine, 1-oxyl-2,2,6,6-tetramethyl-4-(2-hydroxyl-4-oxapentoxy)piperidine, derivatives of said compounds and mixtures thereof.

As used herein, "non-nitroxide-based polymerization retarder," "non-nitroxide-based polymerization inhibitor," or "non-nitroxide-based antioxidant" refers to hindered phenols, quinones, hydroquinones, semi-quinones, catechols, tocopherols, quinone methides, aromatic nitro compounds, aromatic nitroso compounds, aromatic N-nitroso compounds, oximes, hydroxylamines, aromatic diamines, diaromatic amines, non-nitroxide stable free radicals, thiazines, oxazines, and mixtures thereof.

The non-nitroxide-based polymerization retarder may include 2,6-di-t-butylphenol, 4-alkyl-2,64-butylphenol, p-benzoquinone, o-benzoquinone, hydroquinone, hydroquinone methyl ether, t-butylcatechol, vitamin E, 2-(3,5-Di-t-butyl-4-oxocyclohexa-2,5-dien-1-ylidene)acetonitrile, 2,6-di-t-butyl-4-(methoxymethylene)cyclohexa-2,5-dienone), and 4-benzylidene-2,6-di-tert-butylcyclohexa-2,5-dienone, methyl 2-(3,5-di-tert-butyl-4-oxocyclohexa-2,5-dien-1-ylidene)acetate, 2-(3,5-di-t-butyl-4-oxocyclohexa-2,5-dien-1-ylidene)acetic acid, nitrobenzene, nitrophenol, dinitrophenol, 2,4-dinitto-6-s-butylphenol, 2,4-ditro-o-cresol, nitrosobenzene, nitrosophenol, dinitrosophenol, dinitrosotoluene, nitrosophenylhydroxylamine, N,N-diethylhydroxylamine, 1,1'-(hydroxyazanediyl)bis(propan-2-ol), N-isopropylhydroxylamine, p-phenylenediamine, N,N-dialkyl-1,4-phenylenediamine, N,N-diaryl-1,4-phenylenediamine, N-alkyl,N'-aryl-1,4-phenylenediamine, N,N-diphenyl amine, bis(4-octylphenyl)amine, galvinoxyl, diphenyl picrylhydrazyl, phenothiazine, phenoxazine, and structural isomers, derivatives of said compounds and mixtures thereof.

2. SYSTEM FOR MONITORING AND CONTROLLING A RESIDUAL CONCENTRATION OF A NITROXIDE-BASED INHIBITOR IN VINYL-BASED MONOMERS

In an aspect, the present invention is directed to a system for monitoring and controlling a residual concentration of a nitroxide-based inhibitor in vinyl-based monomers. Referring to FIG. 1, the system 10 is in fluid communication with a monomer process column 12 and generally includes a fast flow sampling loop or sampling conditioning fast flow loop 14, and a control module or nitroxide-based inhibitor concentration analyzer (NCA) 18 connected to the fast flow sampling loop 14. The control module 18 controls initial dosage of nitroxide-based inhibitor into the monomer process columns 12, measures residual concentration of nitroxide-based inhibitor in the fast flow sampling loop 14, and provides an optimized dosage of nitroxide-based inhibitor into the monomer process column 12 substantially in real time.

Figure 2:
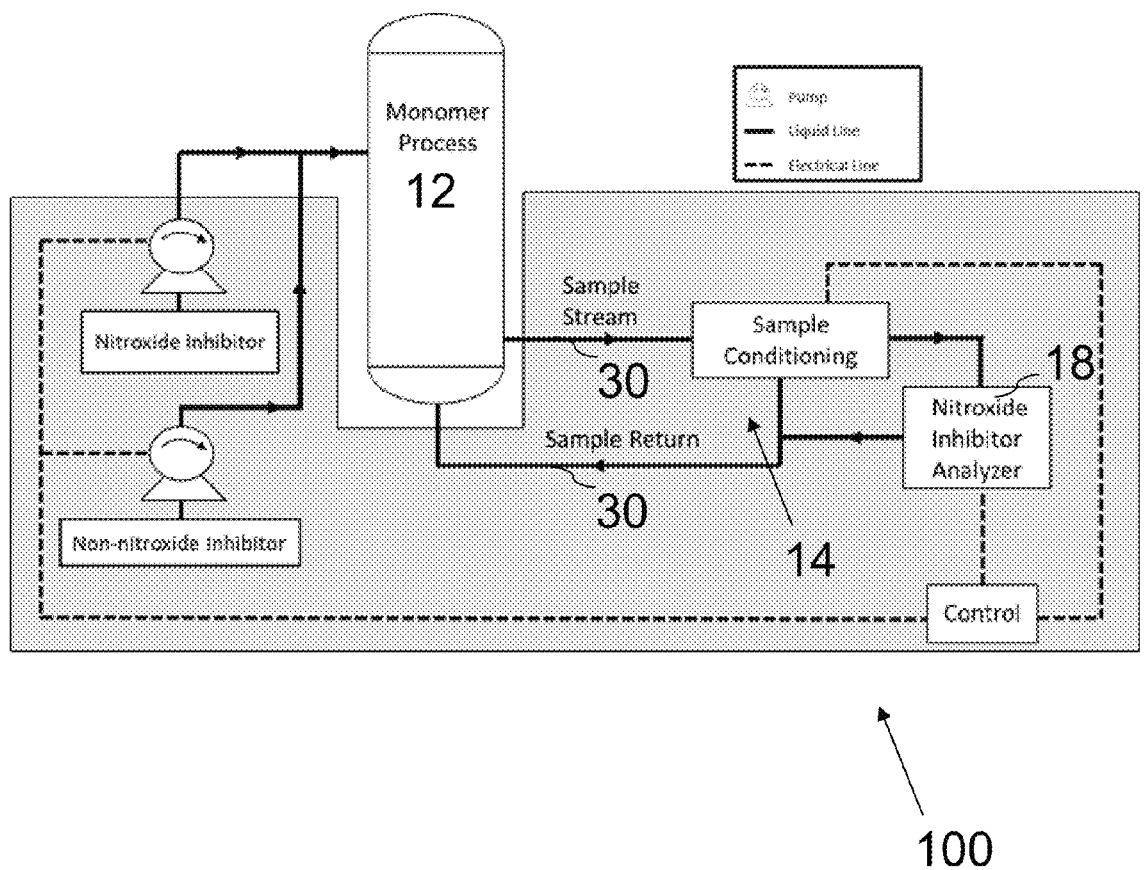
FIG. 2 is a schematic illustration of a system according to another embodiment of the invention.

Referring to FIG. 2, a system 100 according to another embodiment of the invention is schematically illustrated. The control module 18 in this embodiment controls initial dosage of both nitroxide-based inhibitor and non-nitroxide-based inhibitor into the monomer process column 12, measures residual concentration of nitroxide-based inhibitor in the fast flow sampling loop 14, which provides an indirect measure of the non-nitroxide-based inhibitor residual, and provides an optimized dosage of both nitroxide-based inhibitor and non-nitroxide-based inhibitor into the monomer process column 12 substantially in real time.

Figure 3:
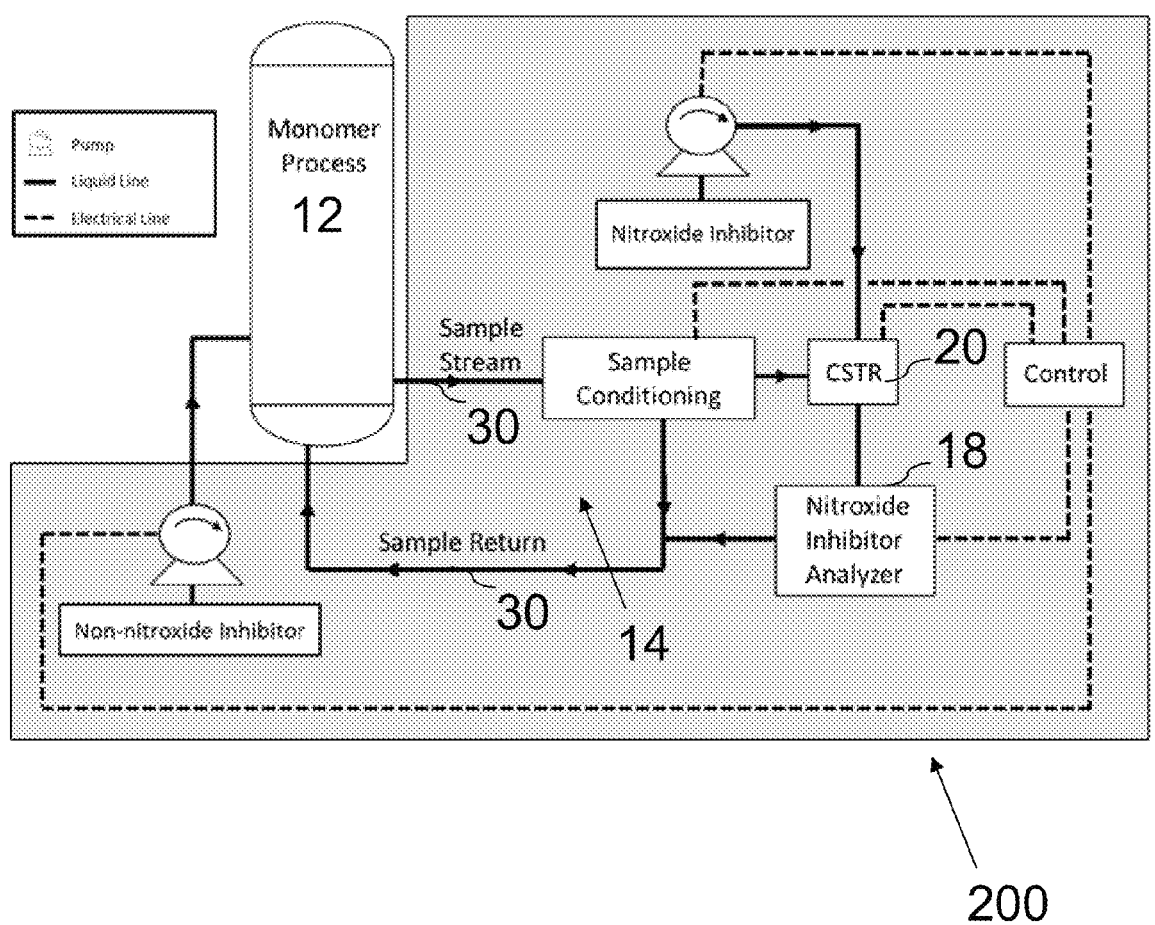
FIG. 3 is a schematic illustration of a system according to yet another embodiment of the invention.

Referring to FIG. 3, a system 200 according to yet another embodiment of the invention is schematically illustrated. The control module 18 in this embodiment is connected to a continuous stirred tank reactor (CSTR) 20, although other structures performing the same function as the CSTR 20 disclosed herein can be used instead. In the illustrated embodiment, the control module 18 controls initial dosage of non-nitroxide-based inhibitor into the monomer process column 12, and collects a sample slipstream into the CSTR 20 where it combines the sample slipstream with a dosage of nitroxide-based inhibitor. The control module 18 then measures residual concentration of nitroxide-based inhibitor in the sample slipstream exiting the CSTR 20, which provides an indirect measure of the non-nitroxide-based inhibitor residual in the process stream and provides an optimized dosage of non-nitroxide-based inhibitor into process stream substantially in real time.

The control module 18 is thus capable of measuring a residual concentration of a nitroxide-based polymerization inhibitor in the vinyl-based monomers, and controlling sampling conditioning through the addition of a nitroxide-based inhibitor in the monomer process columns 12 (see FIGS. 1 and 2) or CSTR 20 (see FIG. 3), substantially in real time. In some embodiments, the control module 18 is connected to the fast flow sampling loop 14 using stainless steel compression fittings such as, for example, available from Swagelok® in Solon, Ohio or Parker in Columbus, Ohio. In other embodiments, however, the control module 18 may be connected to the fast flow sampling loop 14 using any other suitable fittings. Although in some embodiments the system 10, 100, 200 may be a bench-top unit, the systems and methods described herein are not limited in this regard.

Figure 4:
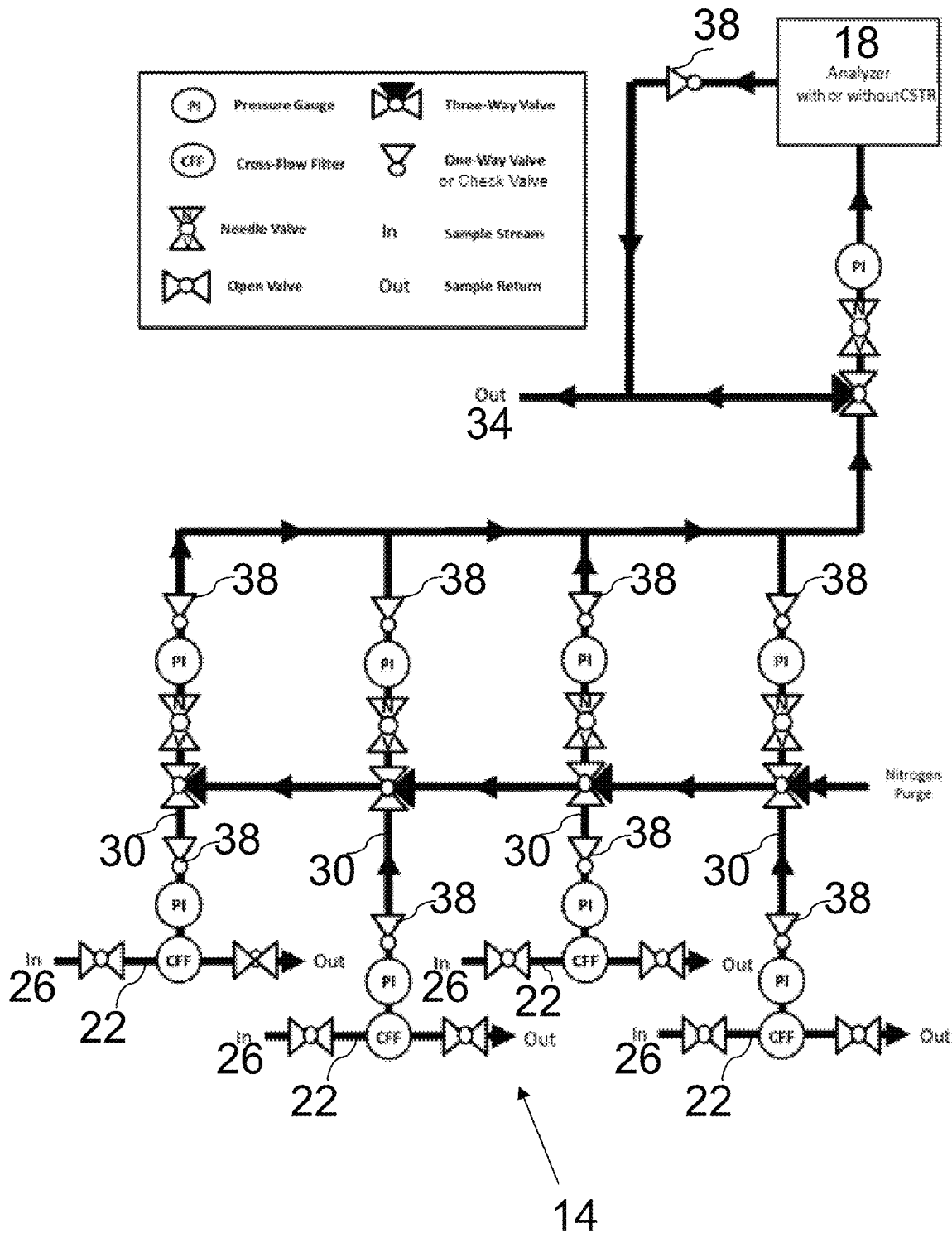
FIG. 4 is a schematic illustration of a fast flow sampling loop and control module of the system of FIGS. 1-3.

Referring also to FIG. 4, the illustrated fast flow sampling loop 14 is designed to receive a process stream 22 through an inlet 26, obtain a sample slipstream 30 from the process stream 22 as the process stream 22 is running, and condition the sample slipstream 30 as desired before flowing it through the control module 18. For example, the sample slipstream 30 may be filtered and the pressure and/or temperature may be adjusted before it flows through the control module 18. The nitroxide-based inhibitor concentration of the sample slipstream 30 is determined by the control module 18, as explained below. After flowing through the control module 18, the sample slipstream 30 is returned to the process stream 22 through an outlet 34. In the illustrated embodiment, the inlet 26, the control module 18, and the outlet 34 are all connected to a respective check valves 38 (e.g., nine in the illustrated embodiment) to facilitate moving the sample slipstream 30 toward a predetermined direction and thereby prevent back pressure and contamination via back flow into the process stream 22. In other embodiments, however, the system 10, 100, 200 may include fewer than all of the check valves 38. In still other embodiments, the system 10, 100, 200 may include additional valves and/or switches depending on the usage requirements or preferences for the particular system 10, 100, 200.

In the illustrated embodiment, the control module 18 includes an electron spin resonance (ESR) spectrometer or a miniaturized or micro electron spin resonance (µESR) spectrometer for analyzing the residual concentration of a nitroxide-based polymerization inhibitor. In other embodiments, however, the control module 18 may instead include or use a gas chromatograph, a gas chromatograph-mass spectrometer, liquid chromatography, nuclear magnetic resonance, x-ray diffraction, x-ray fluorescence, atomic absorption, inductively coupled plasma emission spectroscopy, an ultraviolet-visible spectrometer, an infrared spectrometer, a near-infrared spectrometer, a Raman spectrometer, a fluorometer, a turbidimeter, dynamic light scattering, evaporative light scattering, and/or a titrator. The systems and methods described herein are not limited in this regard. In some embodiments, the polymer content of the sample slipstream is determined separately using a peripheral method (e.g., evaporative light scattering) and correlated to the residual concentration of nitroxide-based inhibitor. In other embodiments, analytical techniques such as titration and turbidimetry may allow for the direct measurement of the polymer content of the sample slipstream in conjunction with these embodiments.

In some embodiments, the control module 18 may further include a manual operator or an electronic device having components such as a processor, memory device, digital storage medium, cathode ray tube, liquid crystal display, plasma display, touch screen, or other monitor, and/or other components. In certain instances, the control module 18 may be operable for integration with one or more application-specific integrated circuits, programs, computer-executable instructions, or algorithms, one or more hard-wired devices, wireless devices, and/or one or more mechanical devices. Some or all of the control module 18 functions may be at a central location, such as a network server, for communication over a local area network, wide area network, wireless network, internet connection, microwave link, infrared link, and the like. In addition, other components such as a signal conditioner or system monitor may be included to facilitate signal-processing algorithms. In some embodiments, the control module 18 can be coupled to any suitable programmable logic controller unit known in the art such as, for example, LABView manufactured by National Instruments in Austin, Tex.

The illustrated ESR spectrometer measures electron resonance signals. In the ESR spectrometer, a sample of a chemical fluid is passed through a radio frequency (RF) or microwave source, while applying a slowly varying magnetic field. In some embodiments, a simple tube may serve as the sample chamber. For example, the sample chamber may be formed out of polytetrafluoroethylene (PTFE) or quartz, and may have an inner diameter from about 3 mm to about 4 mm and an outer diameter from about 5 mm to about 6 mm. Once the sample is received in the sample chamber, the magnetic field is rapidly modulated, and an ESR signal is derived. The ESR signal can indicate the presence of one or more free radicals or molecules and molecular changes thereto in the chemical fluid sample. As explained below, the ESR spectrometer can further be tuned or calibrated to measure the concentration of free radicals in the chemical fluid passed therethrough substantially in real time. In some embodiments, the control module 18 may include a miniaturized ESR spectrometer such as, for example, available from Active Spectrum in Foster City, Calif. In other embodiments, however, the control module 18 may include an ESR spectrometer of any other size. As detailed above, in still other embodiments, the control module 18 may include any other sensors that are capable of measuring a residual concentration of a nitroxide-based polymerization inhibitor substantially in real time.

Figure 5:
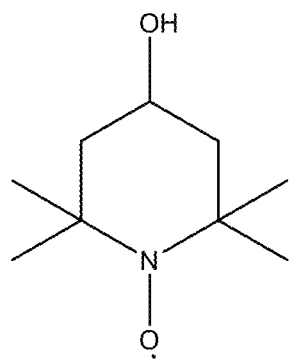
FIG. 5 depicts the molecular structure of the nitroxide-based inhibitor (HTMPO) of FIGS. 1-3.
Figure 6:
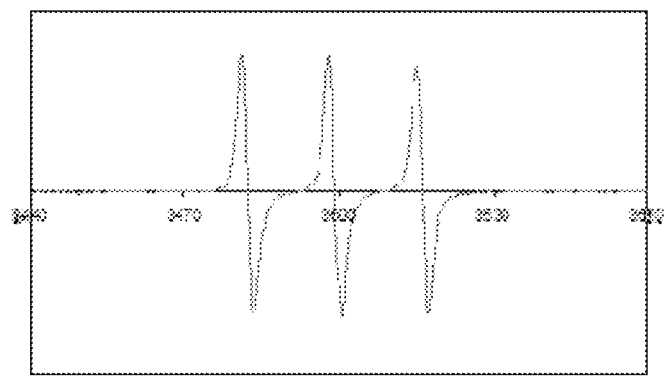
FIG. 6 is a graph plotting an ESR spectrum of the nitroxide-based inhibitor of FIG. 5.

Referring also to FIG. 5, the control module 18 may be tuned or calibrated to have a substantially linear response to the concentration of nitroxide-based polymerization inhibitors such as 2,2,6,6-tetramethyl-4-hydroxypiperidin-1-oxyl (HTMPO). HTMPO is a workhorse molecule used to inhibit undesirable or unwanted polymer formation in the petrochemical industry during manufacturing, processing, and storing of vinyl-based monomers. When passed through the control module 18, the nitroxide-based inhibitor HTMPO can produce the three-line ESR spectrum illustrated in FIG. 6. In other embodiments, the control module 18 may be tuned or calibrated for any other suitable nitroxide-based polymerization inhibitors, such as, for example, the 2,2,6,6-tetramethylpiperidyl-1-oxy radical. The systems and methods described herein are not limited in this regard.

In some embodiments, the integrated area under the ESR signal peaks (see for example FIG. 6) has a substantially linear correspondence to the concentration of the nitroxide-based inhibitor in the sample chamber in ranges of about 1 ppb to about 10,000 ppm. In some embodiments, the linear correspondence is provided to the concentration of the nitroxide-based inhibitor of about 1 ppb or more, about 2 ppb or more, about 3 ppb or more, about 4 ppb or more, about 5 ppb or more, about 6 ppb or more, about 7 ppb or more, about 8 ppb or more, about 9 ppb or more, about 10 ppb or more, about 11 ppb or more, about 12 ppb or more, about 100 ppb or more, about 200 ppb or more, about 300 ppb or more, about 400 ppb or more, about 500 ppb or more, about 600 ppb or more, about 700 ppb or more, about 800 ppb or more, about 900 ppb or more, about 1 ppm or more, about 10 ppm or more, about 20 ppm or more, about 30 ppm or more, about 40 ppm or more, about 50 ppm or more, about 60 ppm or more, about 70 ppm or more, about 80 ppm or more, about 90 ppm or more, about 100 ppm or more, about 200 ppm or more, about 300 ppm or more, about 400 ppm or more, about 500 ppm or more, about 600 ppm or more, about 700 ppm or more, about 800 ppm or more, about 900 ppm or more, about 1,000 ppm or more, about 2,000 ppm or more, about 3,000 ppm or more, about 4,000 ppm or more, about 5,000 ppm or more, about 6,000 ppm or more, about 7,000 ppm or more, about 8,000 ppm or more, or about 9,000 ppm or more. In further embodiments, the linear correspondence is provided to the concentration of the nitroxide-based inhibitor of about 10,000 ppm or less, about 9,000 ppm or less, about 8,000 ppm or less, about 7,000 ppm or less, about 6,000 ppm or less, about 5,000 ppm or less, about 4,000 ppm or less, about 3,000 ppm or less, about 2,000 ppm or less, about 1,000 ppm or less, about 900 ppm or less, about 800 ppm or less, about 700 ppm or less, about 600 ppm or less, about 500 ppm or less, about 400 ppm or less, about 300 ppm or less, about 200 ppm or less, about 100 ppm or less, about 90 ppm or less, about 80 ppm or less, about 70 ppm or less, about 60 ppm or less, about 50 ppm or less, about 40 ppm or less, about 30 ppm or less, about 20 ppm or less, about 10 ppm or less, about 9 ppm or less, about 8 ppm or less, about 7 ppm or less, about 6 ppm or less, about 5 ppm or less, about 4 ppm or less, about 3 ppm or less, about 2 ppm or less, about 1 ppm or less, about 900 ppb or less, about 800 ppb or less, about 700 ppb or less, about 600 ppb or less, about 500 ppb or less, about 400 ppb or less, about 300 ppb or less, about 200 ppb or less, about 100 ppb or less, about 90 ppb or less, about 80 ppb or less, about 70 ppb or less, about 60 ppb or less, about 50 ppb or less, about 40 ppb or less, about 30 ppb or less, about 20 ppb or less, about 12 ppb or less, about 11 ppb or less, about 10 ppb or less, about 9 ppb or less, about 8 ppb or less, about 7 ppb or less, about 6 ppb or less, about 5 ppb or less, about 4 ppb or less, about 3 ppb or less, or about 2 ppb or less. This includes a substantially linear correspondence to the concentration of the nitroxide-based inhibitor in a range of about 12 ppb to about 250 ppm. The ESR spectrometer can thus be calibrated to measure the concentration of free radicals in the chemical fluid passed therethrough substantially in real time.

Figure 7:
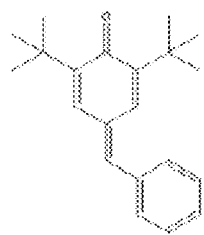
FIG. 7 depicts the molecular structure of the non-nitroxide retarder (Phenyl Quinone Methide).

In some embodiments, the control module 18 may be tuned or calibrated also for non-nitroxide-based polymerization inhibitors or retarders, or antioxidants. Inhibitors or retarders typically offer protection from undesirable polymerization during events such as unintended shutdowns resulting from power failures, where the fast-acting nitroxides would be consumed quickly. During those events, the retarder would still persist and offer protection until further action can be taken. In some embodiments, the control module 18 may be calibrated for non-nitroxide-based polymerization retarders such as phenyl quinone methide (2,6-bis(1,1-dimethylethyl)-4-(phenylenemethylene)cyclohexa-2,5-dien-1-one), as illustrated in FIG. 7, phenols, hydroxylamines, and/or quinone methides. For example, analytical techniques other than ESR spectroscopy (e.g., Gas Chromatography) may be used in conjunction with these embodiments to directly measure the residual concentration of both nitroxide-based inhibitors and non-nitroxide-based inhibitors. Additionally, ESR spectroscopy may be used in conjunction with spin-trapping agents to convert non-nitroxide-based inhibitors into ESR-detectable species. The systems and methods described herein are not limited in this regard.

Figure 8:
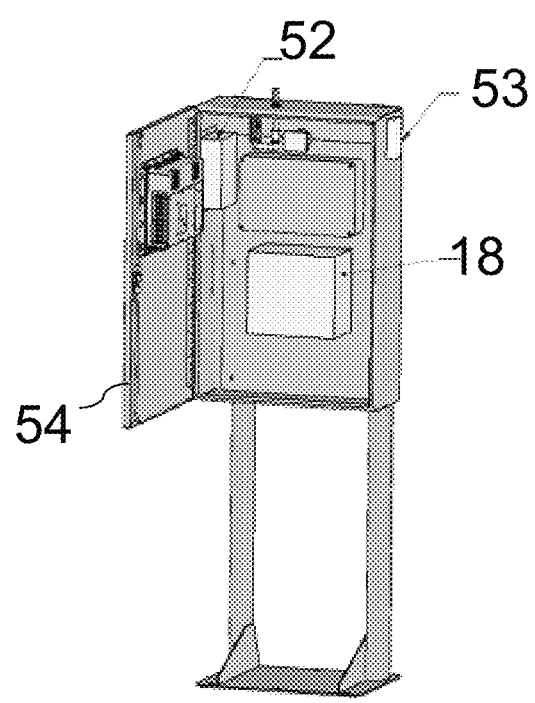
FIG. 8 is a perspective view of an enclosure for the control module of FIGS. 1-3.

Referring also to FIG. 8, the control module 18 may be positioned within an enclosure 50 for field installation in a vinyl-based monomer manufacturing facility. For example, the enclosure 50 may be a Class I/Div II purge box or enclosure that includes a suitable purge system 52, a relief valve 53, and a door 54. In other embodiments, the enclosure 50 may include any other box or enclosure of a suitably rugged construction. The door 54 may optionally include a touchscreen mounted thereto for safe operation.

In some embodiments, the system 10, 100, 200 further includes a nitroxide-based polymerization inhibitor dosing pump (not shown) that is connected to the control module 18, which selectively activates the nitroxide-based polymerization inhibitor dosing pump. The undesirable polymerization of the vinyl-based monomers can thus be controlled during manufacture and purification of the vinyl-based monomers. In further embodiments, the system 100, 200 further includes a non-nitroxide-based retarder dosing pump. In other embodiments, however, dosages of the nitroxide-based polymerization inhibitor and/or the non-nitroxide-based retarder may be provided using any other mechanisms. The systems and methods described herein are not limited in this regard.

3. METHOD OF MONITORING AND CONTROLLING A RESIDUAL CONCENTRATION OF A NITROXIDE-BASED INHIBITOR IN VINYL-BASED MONOMERS

In an aspect, the present invention is directed to a method of monitoring and controlling a nitroxide-based polymerization inhibitor (e.g., 2,2,6,6-tetramethyl-4-hydroxypiperidin-1-oxyl) in vinyl-based monomers. The method includes providing a dosage of the nitroxide-based polymerization inhibitor in the vinyl-based monomers. After the sample slipstream 30 is conditioned in the fast flow sampling loop 14, the control module 18 measures a residual concentration of the nitroxide-based polymerization inhibitor in the sample slipstream 30 substantially in real time. In some embodiments, the residual concentration is measured on a substantially continuous basis. In other embodiments, however, the residual concentration may be measured on a non-continuous basis, e.g., in regular or irregular time intervals. An optimized dosage of the nitroxide-based polymerization inhibitor is provided in response to the measured residual concentration. In some embodiments, the optimized dosage is so determined as to control an undesirable polymerization of the vinyl-based monomer during manufacture and purification thereof.

In some embodiments, the CSTR 20 resides after the fast flow sampling loop 14. The residual concentration of the nitroxide-based inhibitor can then be measured from the contents of the CSTR 20, and the optimized dosage of the nitroxide-based inhibitor can be provided into the CSTR 20. While the control module 18 measures the residual concentration and provides an additional optimized dosage of the nitroxide-based inhibitor, the fast flow sampling loop 14 may be flushed or cleaned with a fresh process stream 26 prior to the next measurement.

In some embodiments, a degree of undesirable polymerization can be evaluated based on the measured residual concentration, as explained below. For example, the degree of undesirable polymerization can be evaluated using at least one of an electron spin resonance spectrometer, a gas chromatograph, a gas chromatograph-mass spectrometer, liquid chromatography, nuclear magnetic resonance, x-ray diffraction, x-ray fluorescence, atomic absorption, inductively coupled plasma emission spectroscopy, an ultraviolet-visible spectrometer, an infrared spectrometer, a near-infrared spectrometer, a Raman spectrometer, a fluorometer, a turbidimeter, dynamic light scattering, evaporative light scattering, and a titrator. In some embodiments, at least one of the co-dosed retarders may be non-nitroxide-based.

The present invention has multiple aspects, illustrated by the following non-limiting examples.

4. EXAMPLES

Figure 9:
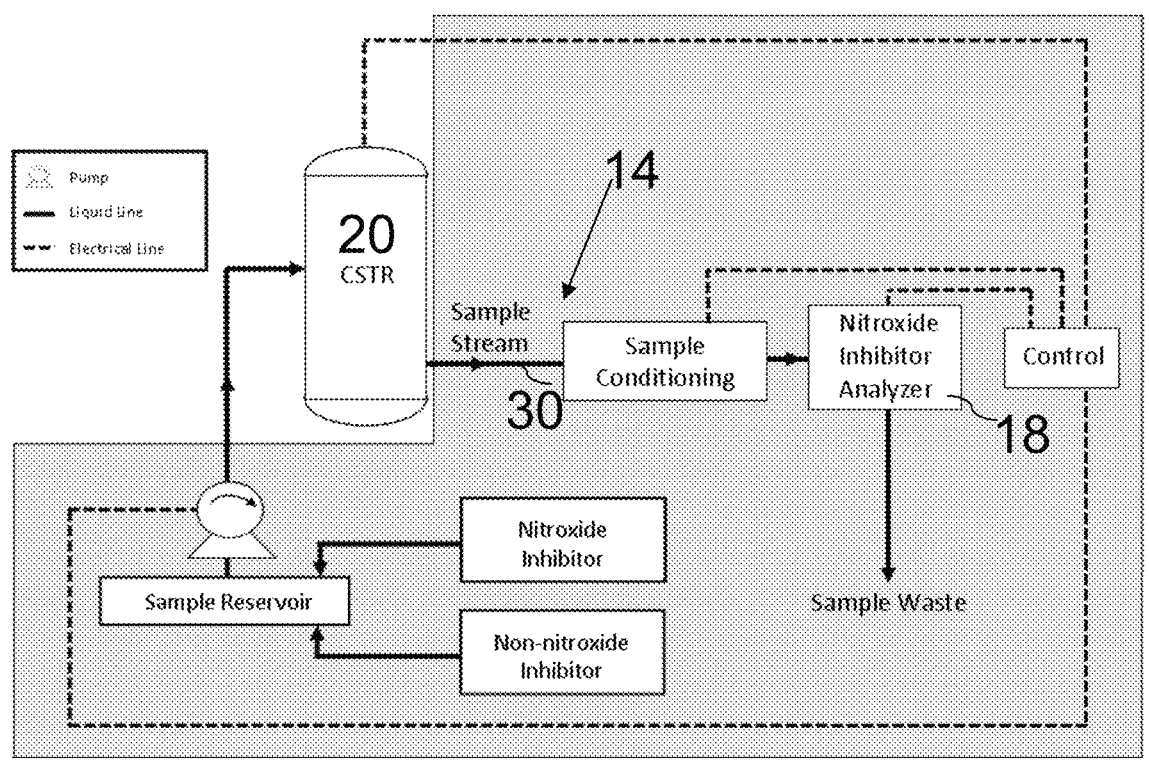
FIG. 9 is a schematic illustration of a benchtop continuous stirred tank reactor configuration used to simulate the system of FIGS. 1-3.

Tests simulating the polymerization of vinyl-based monomers in the process stream 22 during purification (via distillation) and manufacture were conducted in a benchtop continuous stirred tank reactor (CSTR) 20 (see FIG. 9). This test was a dynamic method that simulated the bottom or sump of a distillation column under continuous flow. Parameters of the process stream such as temperature, residence time through the reactor, and the inhibitor concentration could be varied during a run and process stream samples could be evaluated for effects. Styrene (with the commercial inhibitor, tert-butyl catechol (TBC), removed) was chosen as a model vinyl-based monomer system, due to its attractive characteristics such as thermal auto-initiation and reproducible polymerization behavior. The temperatures (105° C.-120° C.) and the relative inhibitor and retarder dosages chosen for these runs were representative of those typically encountered in the bottoms of distillation columns used in Styrene manufacture.

Example 1

Calibration

Figure 10:
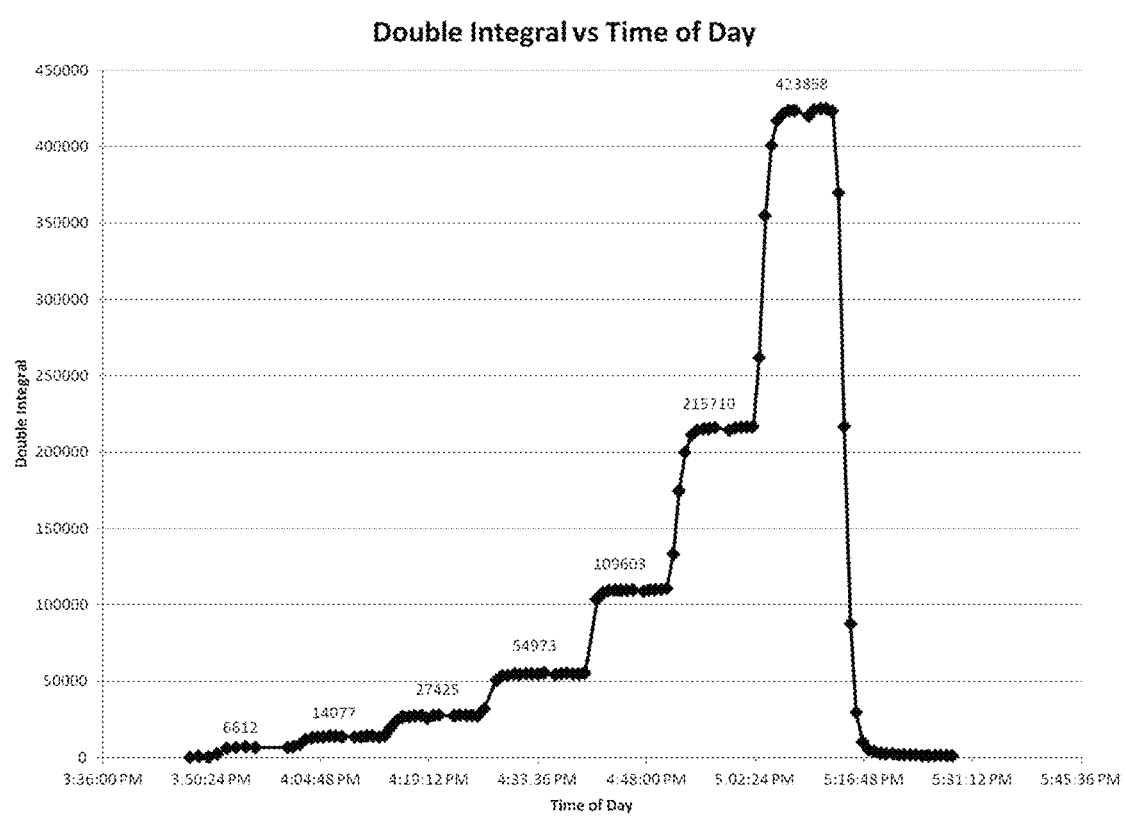
FIG. 10 is a graph plotting a nitroxide signal response against run time during a calibration run in the configuration of FIG. 9.
Figure 11:
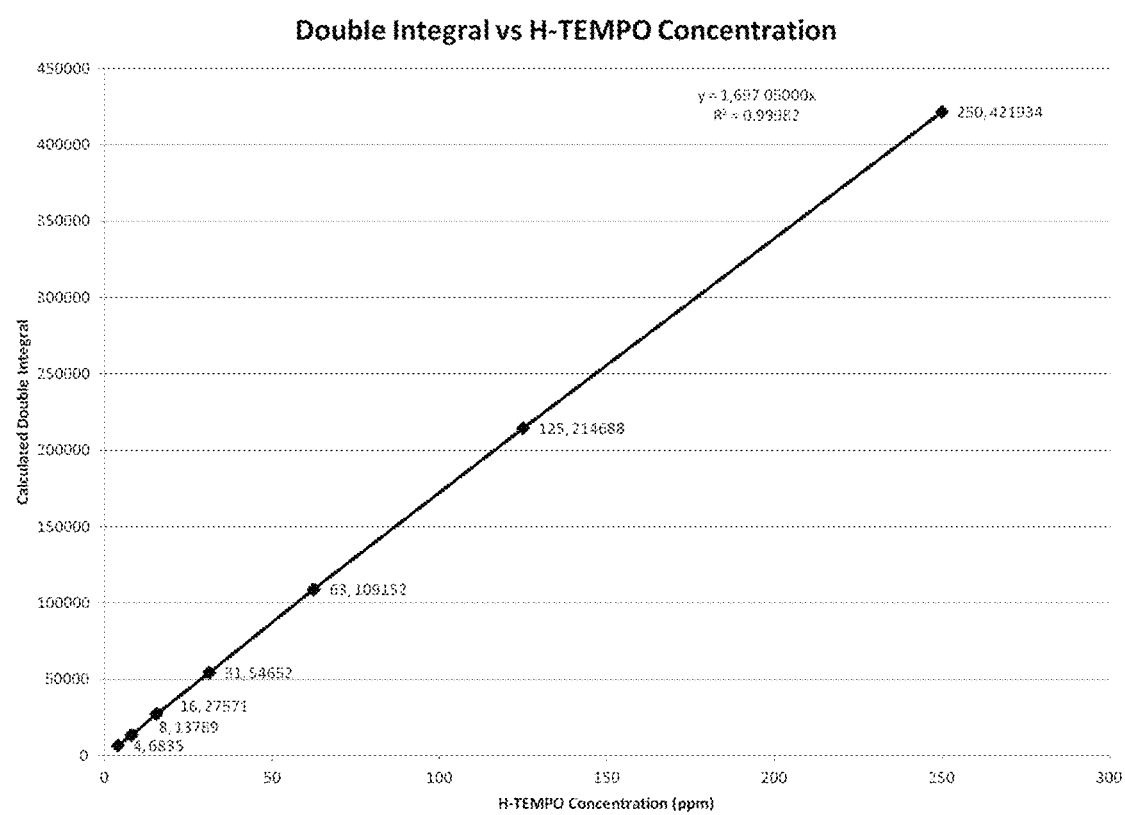
FIG. 11 is a graph plotting a nitroxide signal against nitroxide concentration in the configuration of FIG. 9.

To establish the linearity of signal response of the control module 18 to the concentration of nitroxide-based inhibitors, a calibration run was conducted. Calibration solutions were prepared by dissolving 2,2,6,6-tetramethyl-4-hydroxypiperidin-1-oxyl (HTMPO; see FIG. 5 for molecular structure) in toluene at concentrations ranging from 3.91 ppm to 250 ppm. These solutions were then flowed through the control module 18 in order of increasing concentration at a rate of 1.5 mL/min at room temperature, and ESR spectra were collected continuously at intervals of 47 sec/scan. At the end of the run, pure toluene was run through the control module 18 to rinse out the last calibration solution from the sample chamber, and ESR spectra were also collected during this time. The double integral of the three line spectrum for HTMPO for each scan (see FIG. 6) was taken as the signal response and plotted against the run time during the calibration run (see FIG. 10). This plot demonstrated the response of the control module 18 to changes in the concentration of HTMPO. A calibration curve was constructed by plotting the measured double integrals versus the HTMPO concentration of the calibration solutions (see FIG. 11). This plot established that the signal response of the control module 18 is highly linear to nitroxide concentration with an r-squared of 0.9998.

Example 2

Simulation

Figure 12:
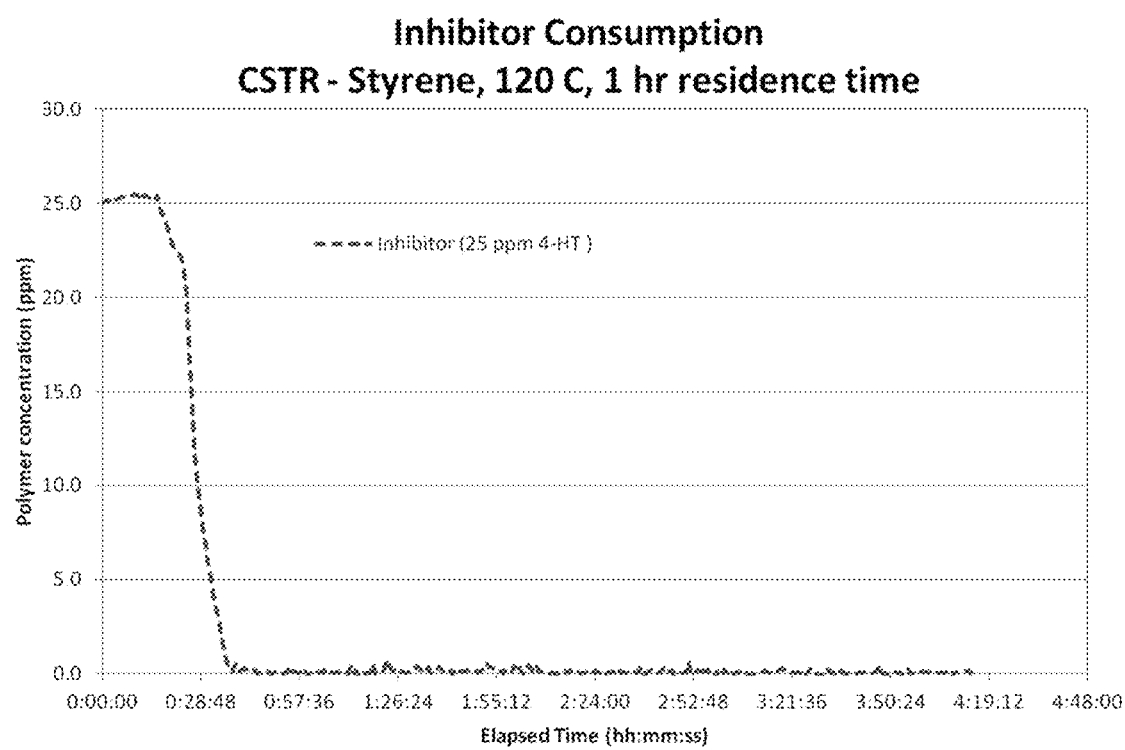
FIG. 12 is a graph plotting a residual HTMPO concentration in the configuration of FIG. 9 run without retarders.
Figure 13:
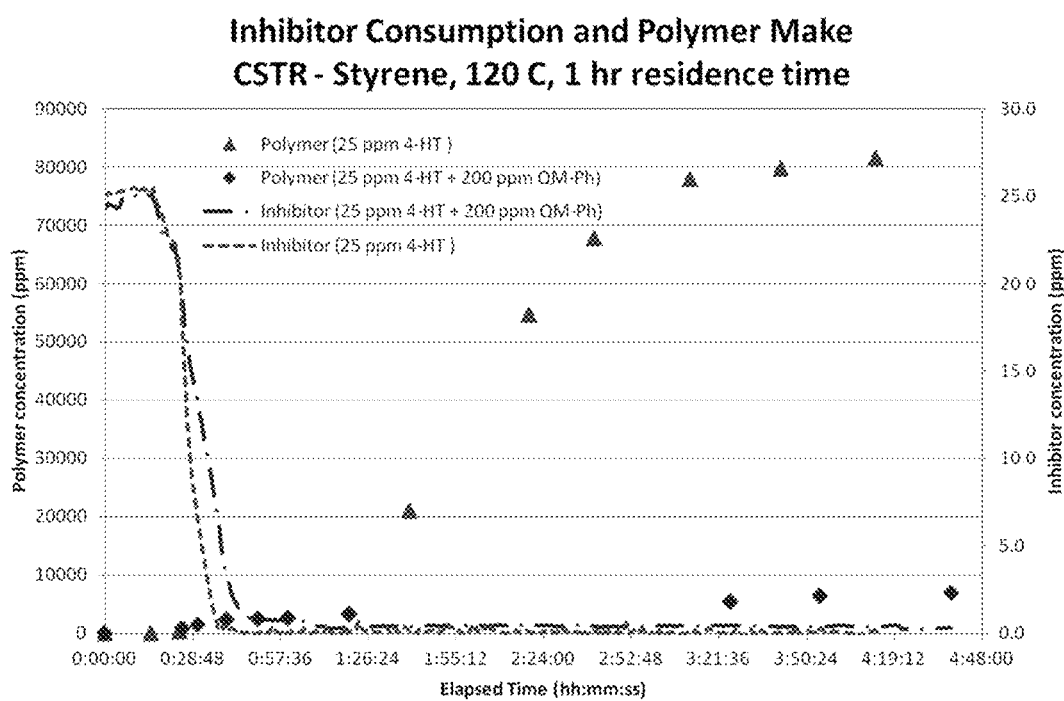
FIG. 13 is a graph plotting a residual HTMPO concentration and polymer make in the configuration of FIG. 9 run with and without retarders.

Two runs were conducted at the same temperature and residence time, comparing the difference between dosing only a nitroxide-based inhibitor and dosing a combination of nitroxide-based inhibitor and non-nitroxide retarder. For the first run, Styrene was used with an initial dosage of 25 ppm HTMPO as the model nitroxide-based inhibitor alone (see FIG. 12). In comparison, for the second run, Styrene was used with initial dosages of 25 ppm HTMPO as the model nitroxide-based inhibitor and 200 ppm Phenyl Quinone Methide as the retarder (see FIG. 13). For both runs, the flow rate was set at 1.5 mL/min, which gave a residence time of 60 min in the CSTR 20, and the temperature of the CSTR 20 was set to 120° C. When this temperature was reached, ESR spectra were collected continuously at intervals of 47 sec/scan for a four hour duration over which the residual concentration of HTMPO was measured. During the course of both runs, samples of the effluent exiting the control module 18 were evaluated for soluble polymer content, which was representative of the extent of undesirable polymerization.

For the inhibitor-only run, the nitroxide concentration decreased from an initial value of 25 ppm to a quantity below the detection limit, taken to be 0 ppm, over 37 minutes. This zero-value residual was maintained throughout the remainder of the four hour run. After the inhibitor was entirely consumed, the corresponding soluble polymer concentration of the process stream drastically increased over the next three hours reaching a plateau in the last hour of around 80,000 ppm.

In contrast, for the inhibitor plus retarder run, the nitroxide decreased from an initial value of 25 ppm to non-zero quantity of 0.7 ppm over 45 minutes, and maintained this non-zero-value residual the remainder of the four hour run. The corresponding soluble polymer concentration of the process stream increased significantly slower but steadily over the next three hours reaching a much lower plateau in the last hour of around 7,000 ppm.

Though not wishing to be bound by a particular theory, given that the temperature, residence time, and initial nitroxide-based inhibitor dosage were identical between the two runs, the only factor that accounts for the considerably decreased rate and quantity of undesirable polymerization (80,000 vs. 7,000 ppm) was the presence of a 200 ppm initial dosage of retarder. The non-nitroxide retarder was not detected by the control module 18. However, its effect was detected by the nitroxide-based inhibitor residual as indicated by the longer time taken to decay from the initial dosage of 25 ppm to a stable residual of 0.7 ppm (45 vs. 37 min) and by the fact that a non-zero residual was achieved under the same severity. These results revealed that the nitroxide-based inhibitor residual can be used as an indirect probe of other undetected factors that can impact undesirable polymerization.

Example 3

Simulation

The process temperature was varied while keeping the initial inhibitor/retarder dosage and residence time constant. Styrene was used with initial dosages of 50 ppm HTMPO as the model nitroxide-based inhibitor and 200 ppm Phenyl Quinone Methide (2,6-bis(1,1-dimethylethyl)-4-(phenylenemethylene)cyclohexa-2,5-dien-1-one; see FIG. 7) as a slower-acting retarder. The flow rate was set at 1.5 mL/min, which gave a residence time of 60 min in the CSTR 20. The initial temperature of the CSTR 20 was set to 105° C., and when this temperature was reached, ESR spectra were collected continuously at intervals of 47 sec/scan for a duration required to measure a stable residual concentration of HTMPO. The temperature was then increased by 5° C. (this increase in thermal severity raises the rate of undesirable polymerization, thereby consuming more inhibitor and lowering the residual), and then spectra were collected until a new stable residual concentration of HTMPO was established. This procedure was performed two more times until a final temperature of 120° C. was reached. Over this period a stepwise drop in the residual HTMPO concentration was observed for each 5° C. increase in temperature (see FIG. 14). These results demonstrated the sensitivity of the control module 18 to temperature-induced changes in nitroxide-based inhibitor concentration.

Figure 14:
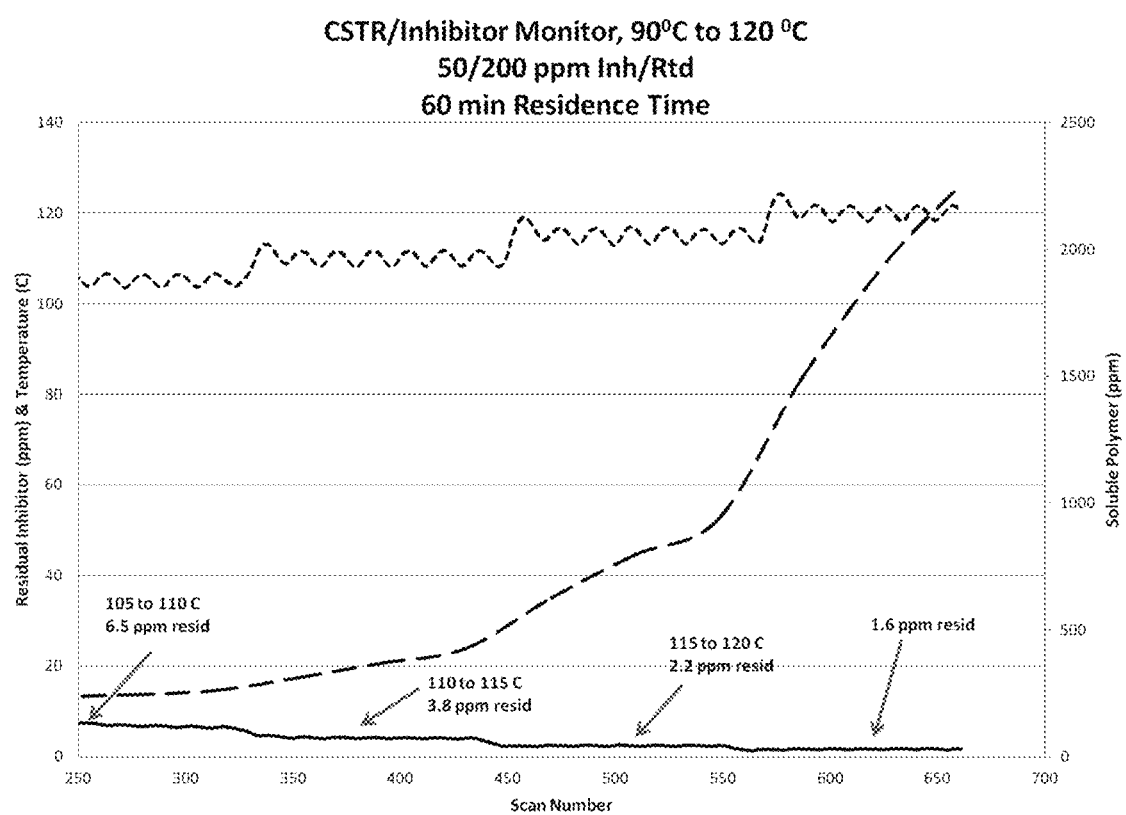
FIG. 14 is a graph plotting an ESR response and soluble polymer measurements to temperature changes in the configuration of FIG. 9.

Referring to FIG. 14, during the course of this run, samples of the effluent exiting the control module 18 were evaluated for soluble polymer content, which was representative of the extent of undesirable polymerization. Upon comparison, it was apparent that as the residual inhibitor concentration decreased with increasing temperature, the soluble polymer content increased.

Example 4

Simulation

The process temperature, the inhibitor/retarder dosage, and the residence time were varied. Again, Styrene was used with initial dosages of 50 ppm HTMPO as the model nitroxide-based inhibitor and 200 ppm Phenyl Quinone Methide as the retarder. However, the initial flow rate was set at 2.0 mL/min, which gave a residence time of 45 min in the CSTR 20. The initial temperature of the CSTR 20 was set to 110° C., and when this temperature was reached ESR spectra were collected continuously at intervals of 47 sec/scan for a duration required to measure a stable residual concentration of HTMPO. The temperature was then increased by 5° C. to 115° C., and then spectra were collected until a new stable residual concentration of HTMPO was established. Over this period a stepwise drop in the residual HTMPO concentration was observed for the increase in temperature (see FIG. 15). The dosage of the HTMPO nitroxide-based inhibitor was then increased to 100 ppm and the dosage of the Phenyl Quinone Methide retarder was increased to 400 ppm. Over this period a stepwise increase in the residual HTMPO concentration was observed. The residence time was then increased to 60 min by lowering the flow rate to 1.5 mL/min. Over this period a stepwise decrease in the residual HTMPO concentration was observed for the longer residence time in the reactor. Finally the dosage of the HTMPO nitroxide-based inhibitor was increased to 125 ppm and the dosage of the Phenyl Quinone Methide retarder was increased to 500 ppm. Over this period a stepwise increase in the residual HTMPO concentration was observed. These results demonstrated the sensitivity of the control module 18 to temperature-, residence time-, and dosage-induced changes in nitroxide-based inhibitor concentration.

Figure 15:
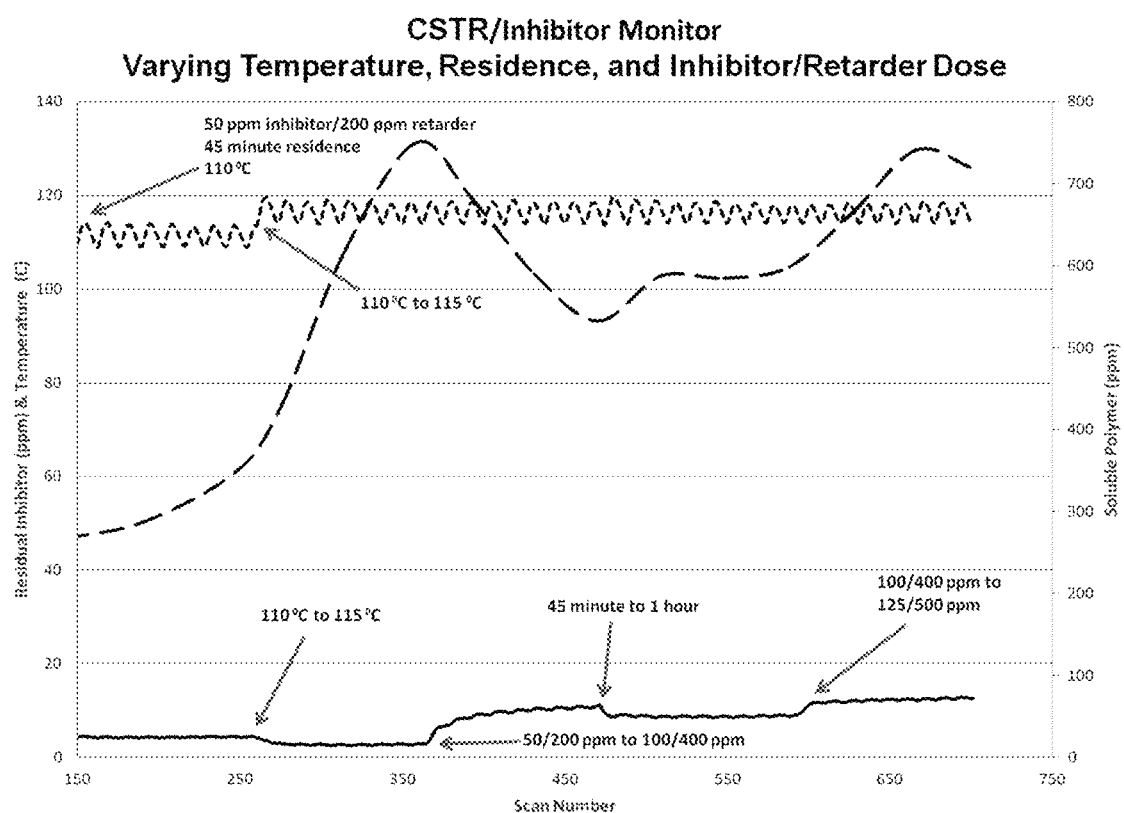
FIG. 15 is a graph plotting an ESR response and soluble polymer measurements to changes in dosage, temperature, and residence time in the configuration of FIG. 9.

Referring to FIG. 15, during the course of this run, samples of the effluent exiting the control module 18 were evaluated for soluble polymer content, which was representative of the extent of undesirable polymerization. Upon comparison, a correlation between soluble polymer concentration and residual inhibitor concentration was observed. As the residual inhibitor concentration decreased with increasing temperature, the soluble polymer content increased. As the residual inhibitor concentration increased with increasing dosage, the soluble polymer content decreased, demonstrating the ability to control the degree of undesirable polymerization by appropriately increasing the dosage of inhibitor additive. As the residual inhibitor concentration decreased with increasing residence time the soluble polymer content increased, simulating that changes in process throughput (i.e., lower flow rate or higher severity) can be detected by changes in the inhibitor residual concentration. However, once again this increase in undesirable polymerization could be controlled by increasing the dosage of inhibitor/retarder, leading to an increased residual inhibitor concentration and a decrease in the soluble polymer content.

It is understood that the foregoing detailed description and accompanying examples are merely illustrative and are not to be taken as limitations upon the scope of the invention, which is defined solely by the appended claims and their equivalents.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method of monitoring and controlling a single nitroxide-based polymerization inhibitor in vinyl-based monomers, the method comprising:
providing a dosage of the single nitroxide-based polymerization inhibitor in the vinyl-based monomers;
measuring a residual concentration of the single nitroxide-based polymerization inhibitor substantially in real time; and
providing an optimized dosage of the single nitroxide-based polymerization inhibitor in response to the measured residual concentration.

2. The method of claim 1, wherein the residual concentration is measured on a substantially continuous basis.

3. The method of claim 1 further comprising providing a fast flow sampling loop, and wherein the residual concentration of the single nitroxide-based inhibitor is measured after the fast flow sampling loop.

4. The method of claim 3, wherein after the fast flow sampling loop resides a continuous stirred tank reactor and an apparatus for providing the optimized dosage of the single nitroxide-based inhibitor into the continuous stirred tank reactor and wherein the residual concentration of the single nitroxide-based inhibitor is measured from the contents of the continuous stirred tank reactor.

5. The method of claim 1 further comprising evaluating a degree of undesirable polymerization in the vinyl-based monomer based on the measured residual concentration.

6. The method of claim 5, wherein the degree of undesirable polymerization is evaluated using at least one of an electron spin resonance spectrometer, a gas chromatograph, a gas chromatograph-mass spectrometer, liquid chromatography, nuclear magnetic resonance, x-ray diffraction, x-ray fluorescence, atomic absorption, inductively coupled plasma emission spectroscopy, an ultraviolet-visible spectrometer, an infrared spectrometer, a near-infrared spectrometer, a Raman spectrometer, a fluorometer, a turbidimeter, dynamic light scattering, evaporative light scattering, and a titrator.

7. The method of claim 5 further comprising co-dosing one or more retarders and/or antioxidants to the vinyl-based monomers and evaluating an effect of the co-dosed retarders and/or antioxidants on the degree of undesirable polymerization based on the measured residual concentration.

8. The method of claim 7, wherein the effect of the co-dosed retarders and/or the antioxidants is evaluated using at least one of an electron spin resonance spectrometer, a gas chromatograph, a gas chromatograph-mass spectrometer, liquid chromatography, nuclear magnetic resonance, x-ray diffraction, x-ray fluorescence, atomic absorption, inductively coupled plasma emission spectroscopy, an ultraviolet-visible spectrometer, an infrared spectrometer, a near-infrared spectrometer, a Raman spectrometer, a fluorometer, a turbidimeter, dynamic light scattering, evaporative light scattering, and a titrator.

9. The method of claim 8, wherein at least one of the co-dosed retarders is non-nitroxide-based.

10. The method of claim 1, wherein the optimized dosage is so determined as to control an undesirable polymerization of the vinyl-based monomer during manufacture and purification thereof.

11. The method of claim 1, wherein the single nitroxide-based polymerization inhibitor is 2,2,6,6-tetramethyl-4-hydroxypiperidin-1-oxyl.

12. A method of monitoring and controlling a nitroxide-based polymerization inhibitor in vinyl-based monomers, the method consisting of:
   providing a dosage of a polymerization inhibitor in the vinyl-based monomers, wherein the polymerization inhibitor consists of a single nitroxide-based polymerization inhibitor;
   measuring a residual concentration of the single nitroxide-based polymerization inhibitor substantially in real time; and
   providing an optimized dosage of the single nitroxide-based polymerization inhibitor in response to the measured residual concentration.

13. The method of claim 1, further comprising evaluating a degree of undesirable polymerization in the vinyl-based monomer based on the measured residual concentration, wherein the degree of undesirable polymerization is evaluated using an electron spin resonance spectrometer.

* * * * *